United States Patent [19]

Gedeon

[11] 4,180,734

[45] Dec. 25, 1979

[54] GAS ANALYZER

[75] Inventor: Andras Gedeon, Täby, Sweden

[73] Assignee: Siemens Aktiengesellschaft, Berlin & Munich, Fed. Rep. of Germany

[21] Appl. No.: 872,449

[22] Filed: Jan. 26, 1978

[30] Foreign Application Priority Data

Feb. 18, 1977 [DE] Fed. Rep. of Germany ....... 2707090

[51] Int. Cl.² .............................. G01J 1/00; G01J 1/42
[52] U.S. Cl. .................................... 250/345; 250/349; 250/373; 128/719
[58] Field of Search .............. 250/338, 339, 343, 345, 250/344, 373, 349; 356/51, 88, 93, 97; 128/2 C

[56] References Cited

U.S. PATENT DOCUMENTS

| 2,806,144 | 9/1957 | Berger et al. | 250/343 |
|---|---|---|---|
| 3,569,696 | 3/1971 | Karlson | 250/344 |
| 3,677,652 | 7/1972 | Little | 250/345 |
| 3,696,247 | 10/1972 | McIntosh et al. | 250/343 |
| 4,067,320 | 1/1978 | Olsson et al. | 128/2 C |

Primary Examiner—Alfred E. Smith
Assistant Examiner—Carolyn E. Fields
Attorney, Agent, or Firm—Hill, Van Santen, Steadman, Chiara & Simpson

[57] ABSTRACT

An illustrative embodiment shows infrared radiation divided into two beams which impinge on respective detectors via respective stationary filters, so as to provide measures of two constituents of a mixture of gases used for mixed anaesthesia. The same angled mirrors which provide the measurement beams may also be reflective on their sides toward the infrared source to provide reference beams to the filters and detectors such that the detectors may alternately sense the measurement and reference beams with the aid of beam interrupters.

2 Claims, 2 Drawing Figures

GAS ANALYZER

BACKGROUND OF THE INVENTION

The invention relates to a gas analyzer having a respiratory tube through which the respiratory gas flows for analysis, a radiation source radiating through the respiratory tube, reflectors which direct the radiation onto radiation receiving means, and several radiation filters, each of which is assigned to a gas.

At the present time halogenated hydrocarbons in gaseous form are used routinely in mixed gases for mixed anaesthesia. Mixed anaesthesia means that sleep is induced by a hypnotic, analgesia (elimination of pain) by an analgesic and muscular relaxation by means of a muscular relaxation agent. Mixed anaesthesia is used frequently in modern hospital care. In practice, when this is carried out the patient is given a gas mixture consisting of three gases, for example oxygen, nitrous oxide, and in addition a halogenated hydrocarbon. Thus the problem arises of measuring the concentrations of the three gases.

A gas analyzer of the initially named kind is known from Canadian Pat. No. 1,000,070. A radiopaque disc with cutout portions is attached to a filter disc which is rotatable by means of a motor. The parts of the filter visible in the cutout portions are permeable with respect to various wave lengths of the received radiation. A filter is assigned to each gas concentration to be metered, which transmits those radiation components which are absorbed by the gas to be measured. The filter portions can be moved in front of a single radiation detector by means of an electric motor which rotates the disc. This gas analyzer, which is bulky and of complicated construction, can only measure different gas concentrations consecutively. Also, it has a relatively high power consumption because of the motor.

SUMMARY OF THE INVENTION

The underlying task of the invention is to devise a gas analyzer of the initially named kind which is compact and of simple construction, which is capable of measuring three gas concentrations simultaneously and which has a low power consumption.

According to the invention this task is solved in that the reflectors of the gas analyzer are so constructed and arranged that the radiation is split into two beams of radiation each of which exits through a window, in that two radiation detectors are present, each of which detects a beam of radiation issuing from the respiratory tube and in that a radiation filter assigned to a specific gas is arranged in each case before each radiation detector. Firstly, two gas concentrations can be measured simultaneously by the two detectors in connection with two filters with different absorption capacities. If the gas to be tested is made up of three constituents, the concentration of the third constituent can then be calculated.

Further objects, features and advantages and details of the invention will be apparent from the following disclosure of an exemplary embodiment which is illustrated in the accompanying sheet of drawings, and from the sub-claims.

DETAILED DESCRIPTION

Figure 1:
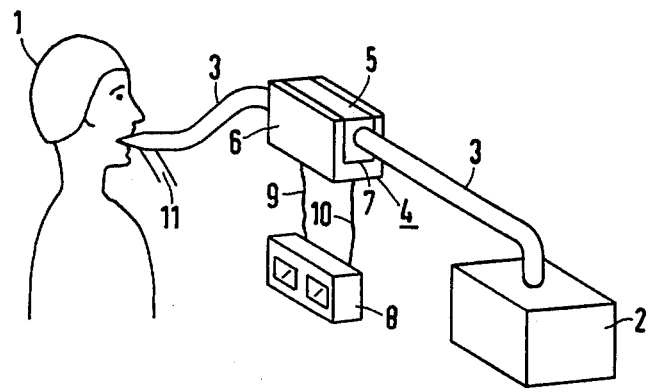
FIG. 1 shows a diagrammatic representation of a gas measuring device for illustrating the invention.

FIG. 1 shows a flexible tubular connection 3 arranged between a patient 1 and a respiratory apparatus 2, for example, an anaesthesia apparatus. During the inhalation phase, the anaesthesia apparatus 2 conducts respiratory gas to the patient 1 via the flexible connection 3. A gas analyzer 4 is disposed in the flexible connection 3 for analyzing the inhaled gases. A respiratory tube 5 which is associated with the gas analyzer 4 is arranged in a detachable manner in a cutout portion 7 of the gas analyzer housing 6. Thus, the respiratory tube 5 may be removed and sterilized. The gas analyzer 4 is connected via connection lines 9, 10 with an indicator device 8 for indicating the gas concentrations to be measured. During the exhalation phases the air flows through the tube 11, the free end of which discharges into the atmosphere.

Figure 2:
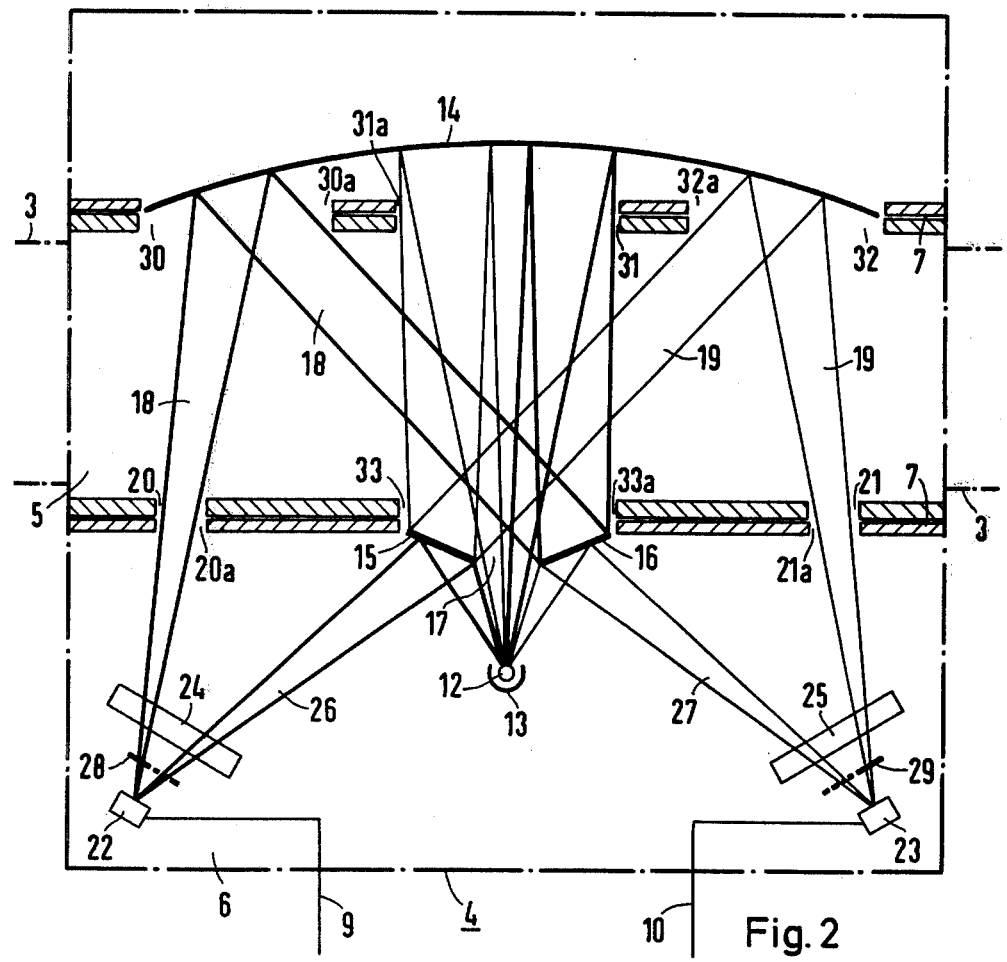
FIG. 2 shows a schematically represented gas analyzer according to the invention.

FIG. 2 illustrates a radiation source 12 which is formed by an infrared radiating ceramic rod. The rays of the radiation source 12 are directed by means of a screen 13. A concave reflector 14 is disposed opposite the radiation source 12. Two plane reflectors 15, 16 which are reflective on both sides are symmetrically fixed opposite the concave reflector 14 at an angle to one another. A clearance 17 is left free between the plane reflectors 15, 16 through which the radiation of the radiation source 12 is focused to a beam of radiation striking the concave reflector 14. The angle of inclination of the plane reflectors 15, 16 is selected so that each of these receives in each case one portion of this beam of radiation after reflection at the concave reflector 14 and reflects it back to the concave reflector 14. In this way, two separate beams of radiation 18, 19 are obtained which exit, after reflection at the concave reflector 14, in each case through a window 20, 21, 20a, 21a in the wall of the respiratory tube 5 and the cutout portion 7. Two radiation detectors 22, 23 are present in the housing 6 of the gas analyzer 4, each of which detects one of the beams of radiation 18, 19 issuing from the respiratory tube 5 via the windows 20, 21, 20a, 21a respectively. In each case a radiation filter 24, 25, assigned to a specific gas, is disposed before each radiation detector 22, 23.

The obliquely arranged reflectors 15, 16 are reflective on both sides. The radiation of the radiation source 12 is also aligned directly onto the sides of the reflectors 15, 16 facing the radiation source. The reflectors 15, 16 are aligned so that they direct the primary radiation of the radiation source 12 in separate beams of radiation 26, 27 onto the detectors 22, 23 via the filters 24, 25, so that in each case a detector 22, 23 is struck by a beam of radiation 26, 27 via the assigned filter 24, 25. An electrically driven radiation interrupter 28, 29 is arranged between each filter 24, 25 and the associated detector 22, 23 and it may be moved periodically from the position marked by a solid line to the position shown by a dotted line and vice versa and thus alternately interrupts the two beams of radiation 18, 19 and 26, 27 striking the detectors 22, 23. The detectors 22, 23 are connected via the connection lines 9, 10 with the indicator device 8 which electrically evaluates the signals of the detectors 22, 23 and gives the reading of the two gas concentrations which correspond to the filters 24, 25.

The walls of the cutout portion 7 and the respiratory tube 5 also have windows 30 to 33 and 30a to 33a which allow the radiation of the radiation source 12 to pass through at the required locations.

FIG. 2 clearly shows that the respiratory tube 5 may be removed easily from the cutout portion 7 and that the gas analyzer 4 thus forms a unit distinct from the respiratory tube 5.

By way of example, FIG. 2 shows a housing 6 with a square cross section cutout portion 7. The square cross section tube 5 slides axially into the cutout portion 7, so that when tube 5 is in assembled relation as shown in FIG. 2, the housing 6 provides a lightproof chamber surrounding the tube 5. The infrared transmissive windows at 20, 21, and 30–33 of tube 5 may seal the tube 5 gas tight except for its flow communication with the connecting tube 3 (as indicated by the dot-dash lines referenced by the numeral 3 in FIG. 2). Cutout portion 7 is defined by a tubular wall of square cross section surrounding tube 5 on its four sides and provided with infrared transmissive windows 20a, 21a, 30a–33a, aligned with the corresponding windows of tube 5 as shown in FIG. 2. In this case respiratory tube 5 is removable in an axial direction from the cutout portion 7 of housing 6 for sterilization.

It will be apparent that many modifications and variations may be effected without departing from the scope of the novel concepts and teachings of the present invention.

I claim as my invention:

1. A gas analyzer having a respiratory tube through which the respiratory gas flows for analysis, a radiation source which radiates through the respiratory tube, radiation receiving means, reflector means which direct the radiation onto the radiation receiving means, and several radiation filters, each of which is assigned to one gas, characterized in that the reflector means (14, 15, 16) are constructed and arranged so that the radiation is divided into two beams of radiation (18, 19) each of which exits through a window (20, 21, 20a, 21a), that the receiving means comprises two radiation detectors (22, 23), each of which detects one beam of radiation (18, 19) issuing from the respiratory tube (5), and that the radiation filters (24, 25), each assigned to a specific gas, are arranged in each case before a respective one of the radiation detectors (22, 23), and further characterized in that the reflector means comprises concave reflector means (14) disposed opposite the radiation source (12), and two obliquely arranged plane reflectors (15, 16) lying symmetrically at an angle to one another opposite the concave reflector means (14), that a clearance (17) is left between the plane reflectors (15, 16) through which the radiation of the radiation source (12) is focused to a beam of radiation striking the concave reflector means (14) and that the angle of inclination of the plane reflectors (15, 16) is selected so that they each reflect a portion of the beam of radiation after reflection at the concave reflector means (14), in each case through a window (20, 21).

2. A gas analyzer having a respiratory tube through which the respiratory gas flows for analysis, a radiation source which radiates through the respiratory tube, radiation receiving means, reflector means which direct the radiation onto the radiation receiving means, and several radiation filters, each of which is assigned to one gas, characterized in that the reflector means (14, 15, 16) are constructed and arranged so that the radiation is divided into two beams of radiation (18, 19) each of which exits through a window (20, 21, 20a, 21a), that the receiving means comprises two radiation detectors (22, 23), each of which detects one beam of radiation (18, 19) issuing from the respiratory tube (5), and that the radiation filters (24, 25), each assigned to a specific gas, are arranged in each case before a respective one of the radiation detectors (22, 23), and further characterized in that the reflector means comprises concave reflector means (14) disposed opposite the radiation source (12), and two obliquely arranged plane reflectors (15, 16) lying symmetrically at an angle to one another opposite the concave reflector means (14), that a clearance (17) is left between the plane reflectors (15, 16) through which the radiation of the radiation source (12) is focused to a beam of radiation striking the concave reflector means (14) and that the angle of inclination of the plane reflectorv (15, 16) is selected so that they each reflect a portion of the beam of radiation after reflection at the concave reflector means (14), in each case through a window (20, 21), and further characterized in that the obliquely arranged reflectors (15, 16) are reflective on both sides, that the radiation of the radiation source (12) is also aligned directly onto the side of the reflectors (15, 16) which is facing the radiation source (12), and the reflectors (15, 16) are aligned so that they direct this primary radiation in separate beams of radiation (26, 27) via the filters (24, 25) onto the detectors (22, 23) so that each detector (22, 23) is struck by a beam of radiation (26, 27) via the assigned filter (24, 25), and that a radiation interrupter (28, 29) is disposed before each detector (22, 23) which alternately interrupts the two beams of radiation (18, 19, and 26, 27) striking the detectors (22, 23).

* * * * *